United States Patent [19]

VandenBerg

[11] Patent Number: Plant 7,519

[45] Date of Patent: May 7, 1991

[54] CHRYSANTHEMUM PLANT NAMED CANELA

[75] Inventor: Cornelis P. VandenBerg, Salinas, Calif.

[73] Assignee: Yoder Brothers, Inc., Barberton, Ohio

[21] Appl. No.: 469,308

[22] Filed: Jan. 24, 1990

[51] Int. Cl.[5] ..... A01H 5/00

[52] U.S. Cl. ..... Plt./79

[58] Field of Search ..... Plt./74, 78, 79

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Canela particularly characterized by its flat capitulum form; anemone capitulum type; bronze ray floret color; diameter across face of capitulum of 64 to 80 mm when fully opened, with anemone cushion diameter of 23 to 26 mm; photoperiodic flowering response to short days of 53 to 57 days when grown in Salinas, Calif., and 66 to 70 days when grown in Bogota, Colombia; peduncle length of the first lateral of 13 to 15 cm, and of the fourth lateral of 18 to 23 cm, when grown without growth regulator applications, on open, terminal sprays; plant height of 84 to 91 cm when grown as a single stem spray cut mum in Salinas, Calif. with 6 to 7 long days prior to start of short days, and a height of 97 to 102 cm when grown in Bogota, Colombia with 14 to 15 long days prior to start of short days; and excellent tolerance to low night temperatures for bud initiation and flower development.

3 Drawing Sheets

1

The present invention comprises a new and distinct cultivar of Chrysanthemum, botanically known as *Dendranthema grandiflora,* and referred to by the cultivar name Canela.

Canela, identified as 84-185012, was originated from a cross made by Cornelis P. VandenBerg in a controlled breeding program in Salinas, Calif., in 1983.

The female parent of CAnela was an unnamed seedling, identified as 78-546013, and described as a pink daisy cut spray mum. The male parent of Canela was an unnamed seedling, identified as 78-19015, and described as a white anemone cut spray mum.

Canela was discovered and selected as one flowering plant within the progeny of the stated cross by Cornelis P. VandenBerg in October 1984, in a controlled environment in Salinas, Calif.

The first act of asexual reproduction of Canela was accomplished when vegetative cuttings were taken from the initial selection in December 1984 in a controlled environment in Salinas, Calif., by technicians working under the supervision of Cornelis P. VandenBerg.

Horticultural examination of controlled flowerings of successive plantings has shown that the unique combination of characteristics as herein disclosed for Canela are firmly fixed and are retained through successive generations of asexual reproduction.

Canela has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

2

The following observations, measurements and comparisons describe plants grown in Salinas, Calif. and in Bogota, Colombia under greenhouse conditions which approximate those generally used in commercial greenhouse practice. The low night temperature tolerance was determined in repeated flowerings in Bogota, Colombia.

The following traits have been repeatedly observed and are determined to be basic characteristics of Canela, which, in combination, distinguish this Chrysanthemum as a new and distinct cultivar:

1. Flat capitulum form.
2. Anemone capitulum type.
3. Bronze ray floret color.
4. Diameter across face of capitulum of 64 to 80 mm when fully opened, with an anemone cushion diameter of 23 to 26 mm.
5. Flowering response in Salinas under normal temperatures is 53 to 57 days after start of short days. Flowering response in Bogota, Colombia under minimum 7 degrees Celsius night and maximum 29 degrees Celsius day is 66 to 70 days after start of short days.
6. Peduncle length of the first lateral at flowering after removing the apical bud without growth regulator applications is 13 to 15 cm when grown in Salinas, Calif., and 13 to 15 cm when grown in Bogota, Colombia. Peduncle length of the fourth lateral at flowering is 18 to 23 cm when grown in Salinas, and 20 to 23 cm when grown in Bogota.
7. Plant height is 84 to 91 cm when grown in Salinas with 6 to 7 long days prior to start of short days, and the height is 97 to 102 cm when grown in Bogota with 14 to 15 long days prior to start of short days.
8. Excellent tolerance to low night temperatures for bud initiation and flower development. Average minimum low night temperatures in our Bogota trials ranged from 7 to 8.5 degrees Celsius.

The above measurements represent repeated flowerings over a period of a minimum of two years.

The accompanying photographic drawings show typical inflorescence and leaf characteristics of Canela, with the colors being as nearly true as possible with illustrations of this type.

Sheet 1 is a color photograph of Canela grown as a single stem cut spray mum.

Sheet 2 is a black and white photograph of three views of the inflorescence of Canela.

Sheet 3 is a black and white photograph showing the upper and under sides of the leaves of Canela at three stages of development (mature, intermediate and immature).

Of the cultivars known to the inventor, the most similar in comparison to Canela is the cultivar identified as Leona, described as a bronze anemone spray cut mum, disclosed in U.S. plant patent application Ser. No. 359,922, now U.S. Plant Pat. No. 7,315. Reference is made to attached Chart A, which compares certain characteristics of Canela to the same characteristics of Leona. Because of its marginal low night temperature tolerance, Leona is not being grown in Bogota, Colombia, and Chart A accordingly shows no measurements of Leona at that location.

Similar traits are capitulum form and type, spray formation, and peduncle length. Plant height of both cultivars is comparable. Canela has a smaller diameter of capitulum, a longer flowering response to short days, and a better low night temperature tolerance. In addition, the ray floret color of Canela is a blend of different shades of bronze, while the primary ray floret color of Leona is a more uniform, much lighter yellow-orange, overcast with bronze. The respective colors are significantly different although both are in the general bronze category.

In the following description color references are made to The Royal Horticultural Society Colour Chart. Because of the blend of different shades of bronze in each flower, a precise description of the ray floret color is extremely difficult. The values given are those believed to be closest to the actual color of Canela. The color values were determined on plant material grown in Salinas, Calif. on Aug. 2, 1989.

Classification:

*Botanical.*—*Dendranthema grandiflora* cv Canela.

*Commercial.*—Anemone cut spray mum.

INFLORESCENCE

A. Capitulum:

*Form.*—Flat.

*Type.*—Anemone.

*Diameter across face.*—64 to 80 mm when fully opened.

B. Corolla of ray florets:

*Color (general tonality from a distance of three meters).*—Bronze.

*Color (upper surface).*—When fully opened, 163B, tinged and streaked with 171B. Color of flower buds are very dark, closest to 178A to 178B.

*Color (under surface).*—163B to 163C, streaked with 171B to 171C.

*Shape.*—Straight, flat, oblong.

C. Corolla of disc florets (Anemone cushion):

*Color (mature).*—Closest to 14A, tinged and streaked with 171B.

*Color (immature).*—151A to 151B, tinged with 171B.

D. Reproductive organs:

*Androecium.*—Present on disc florets only; no pollen.

*Gynoecium.*—Present on both ray and disc florets.

PLANT

A. General appearance:

*Height.*—84 to 91 cm when grown as a single stem cut mum with 6 to 7 long days prior to start of short days in Salinas, Calif.; 97 to 102 cm when grown as a single stem cut mum with 14 to 15 long days prior to start of short days in Bogota, Colombia.

B. Foliage:

*Color (upper surface).*—147A.

*Color (under surface).*—147B.

*Shape.*—See photograph.

CHART A

COMPARISON OF CANELA AND LEONA

| CHARACTERISTIC | CANELA | LEONA |
|---|---|---|
| Ray floret color | Bronze | Light bronze |
| Capitulum form | Flat | Flat |
| Capitulum type | Anemone | Anemone |
| Spray formation | Terminal | Terminal |
| Peduncle length | | |
| 1st lateral, Salinas | 13 to 15 cm | 13 to 15 cm |
| 4th lateral, Salinas | 18 to 23 cm | 18 to 23 cm |
| 1st lateral, Bogota | 13 to 15 cm | Not available |
| 5th lateral, Bogota | 20 to 23 cm | Not available |
| Diameter across face of capitulum | 64 to 80 mm | 76 to 89 mm |
| Plant height | | |
| 6–7 long days, Salinas | 84 to 91 cm | 81 to 89 cm |
| 14–15 long days, Bogota | 97 to 102 cm | Not available |
| Flowering response period | | |
| in Salinas | 53 to 57 days | 44 to 49 days |
| in Bogota | 66 to 70 days | Not available |
| Low night temperature tolerance | Excellent | Marginal |

Comparisons Made of Plants Grown as Single Stem Spray Cut Mums in Salinas, California, and Characteristics of Plants of Canela Grown in Bogota, Colombia

I claim:

1. A new and distinct Chrysanthemum plant named Canela, as described and illustrated.

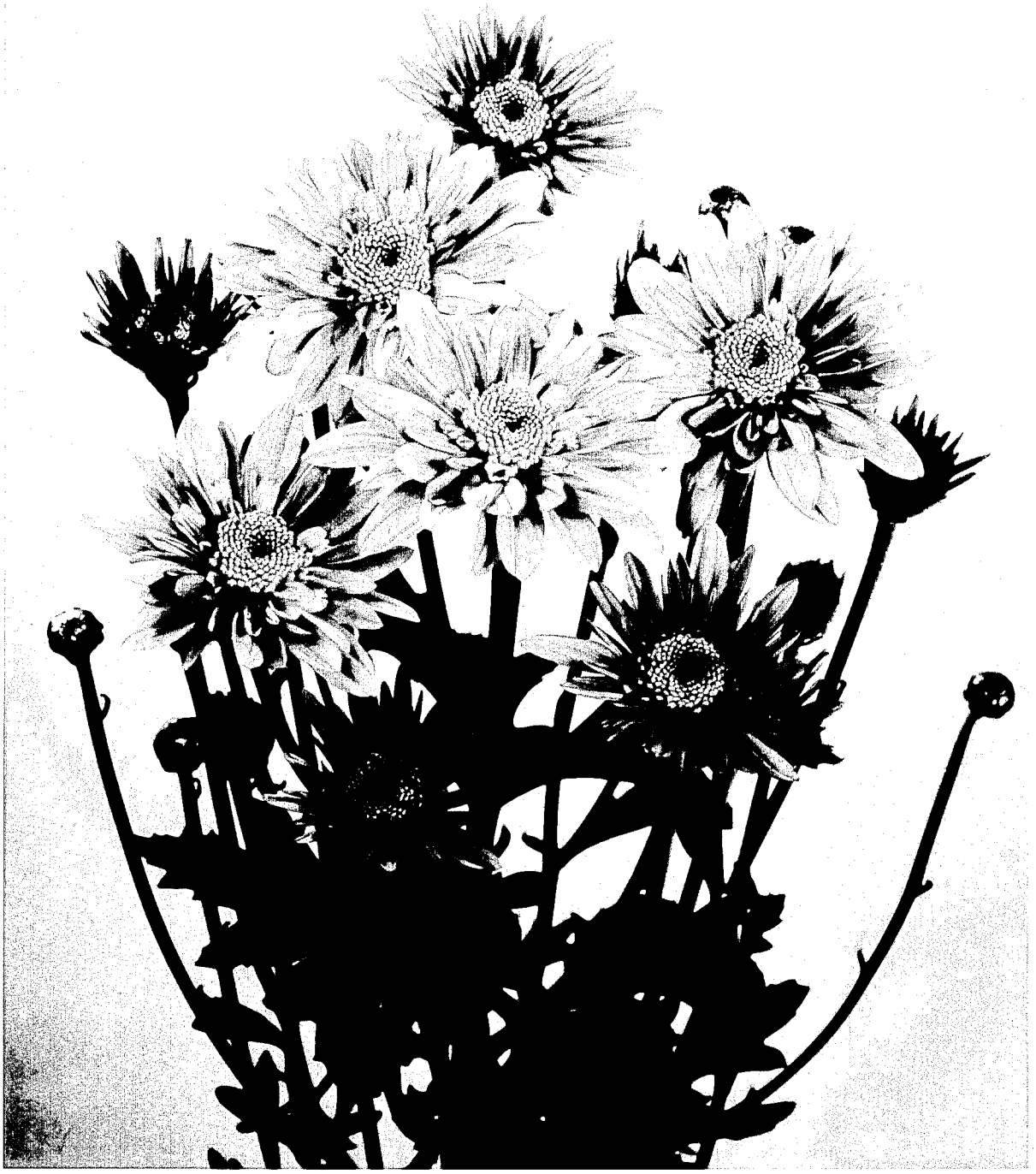

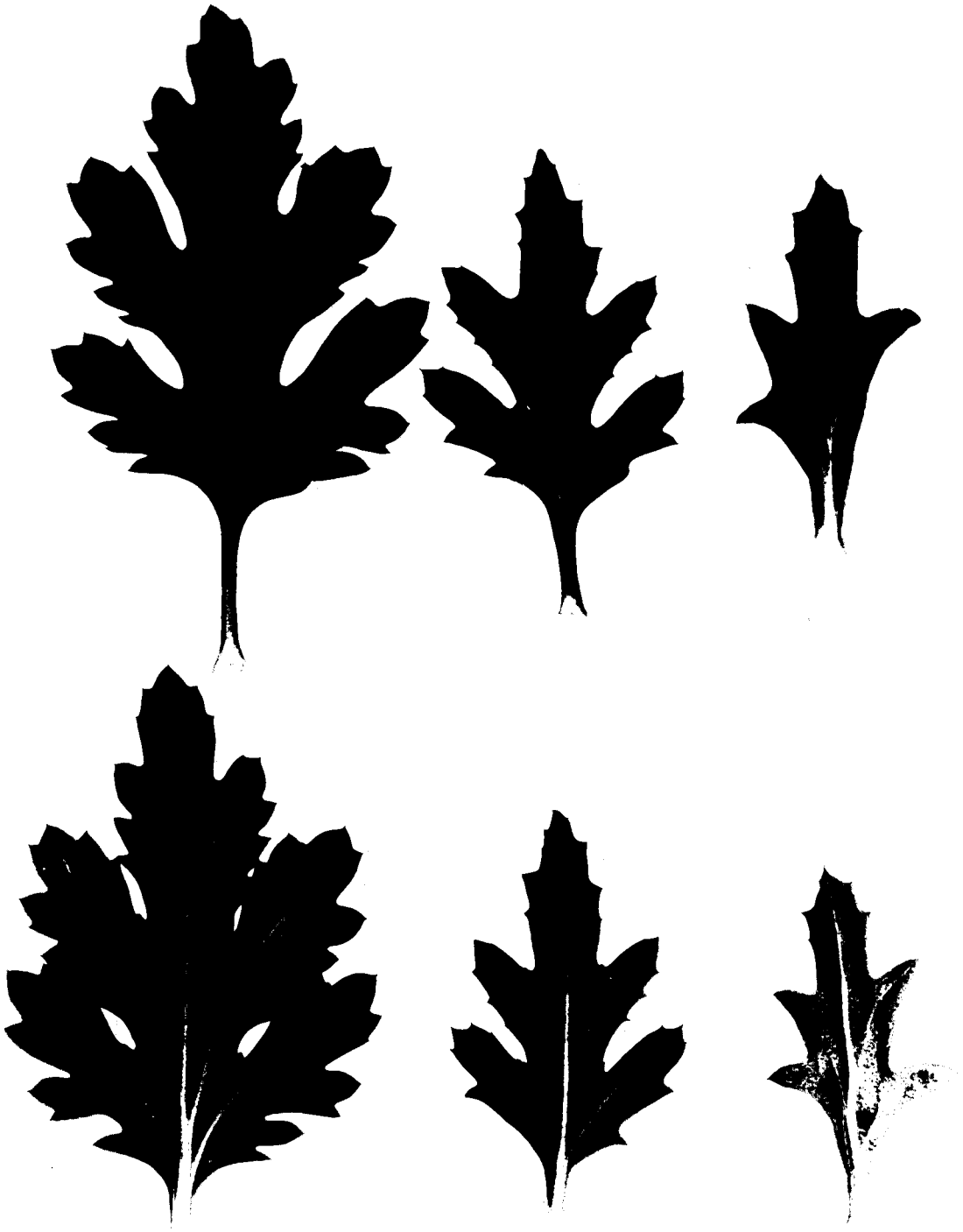

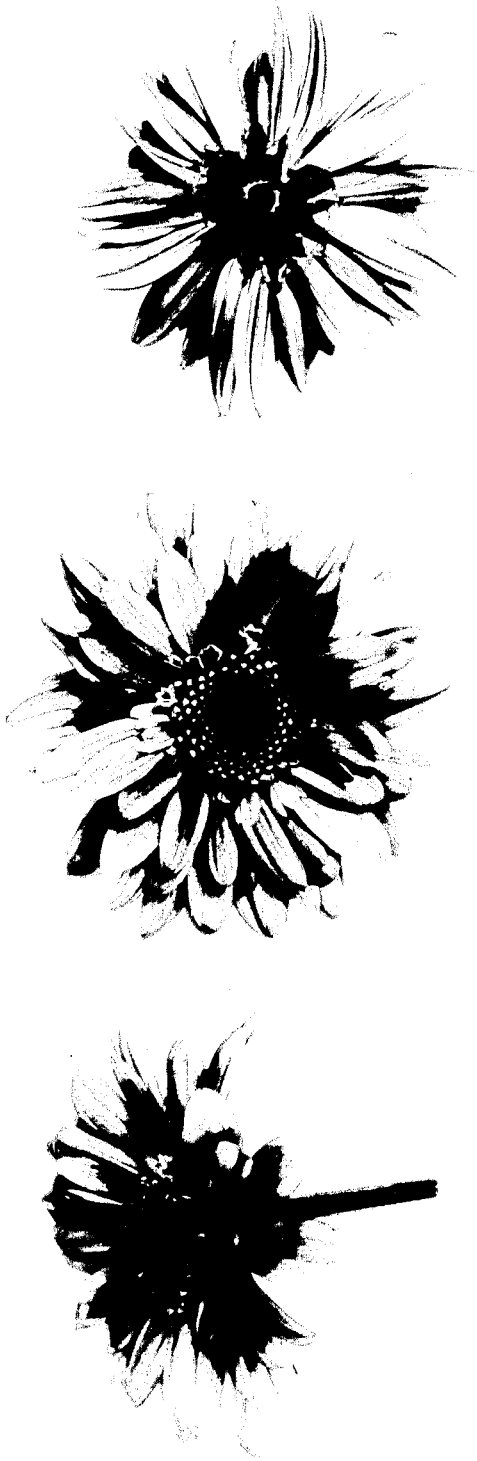

* * * * *